(12) United States Patent
Duquette et al.

(10) Patent No.: US 8,210,182 B2
(45) Date of Patent: Jul. 3, 2012

(54) CONTINUOUS POSITIVE AIRWAY PRESSURE DEVICE

(75) Inventors: Steven Duquette, Laguna Niguel, CA (US); Steve Han, Upland, CA (US)

(73) Assignee: CareFusion 207, Inc., San Diego, CA (US)

( * ) Notice: Subject to any disclaimer, the term of this patent is extended or adjusted under 35 U.S.C. 154(b) by 1101 days.

(21) Appl. No.: 11/966,805

(22) Filed: Dec. 28, 2007

(65) Prior Publication Data

US 2009/0165799 A1 Jul. 2, 2009

(51) Int. Cl.
*A61M 15/08* (2006.01)
*A62B 18/02* (2006.01)
*A61M 16/00* (2006.01)

(52) U.S. Cl. ......... 128/207.18; 128/207.13; 128/206.21; 128/200.26; 128/200.24

(58) Field of Classification Search .................. 128/848, 128/857, 863, 200.24, 200.26, 203.22, 204.18, 128/204.21, 205.2, 5, 206.21, 206.24, 206.27, 128/207.11, 207.13, 207.18
See application file for complete search history.

(56) References Cited

U.S. PATENT DOCUMENTS

| | | | | |
|---|---|---|---|---|
| 4,782,832 A * | 11/1988 | Trimble et al. | ......... | 128/207.18 |
| 4,915,105 A * | 4/1990 | Lee | ......... | 128/205.27 |
| 5,193,532 A | 3/1993 | Moa | | |
| 6,581,601 B2 * | 6/2003 | Ziaee | ......... | 128/206.21 |
| 6,626,177 B1 * | 9/2003 | Ziaee | ......... | 128/206.21 |
| 7,578,294 B2 * | 8/2009 | Pierro et al. | ......... | 128/207.13 |
| 7,874,293 B2 * | 1/2011 | Gunaratnam et al. | ... | 128/207.18 |
| 2003/0200970 A1 * | 10/2003 | Stenzler et al. | ......... | 128/207.18 |
| 2004/0065330 A1 | 4/2004 | Landis | | |
| 2005/0011524 A1 * | 1/2005 | Thomlinson et al. | .... | 128/207.18 |
| 2007/0074724 A1 | 4/2007 | Duquette | | |
| 2010/0252044 A1 * | 10/2010 | Duquette et al. | ......... | 128/204.25 |

FOREIGN PATENT DOCUMENTS

| | | |
|---|---|---|
| JP | 2007-527271 | 9/2007 |
| WO | WO-2007/040828 | 4/2007 |
| WO | WO-2007/064668 | 6/2007 |

OTHER PUBLICATIONS

A. Lichtarowicz et al., Fourth Cranfield Fluidics Conference Mar. 17-20, 1970, held at the University of Warwick, Coventry, England, Paper B5, "Characteristics of Jet-Pipe Valves".
Web site www.flometrics.com/services/ncpap/, Flometrics Product Engineering Specializing in Fluid Dynamics and Thermodynamics, retrieved from web site Apr. 26, 2007.
Hiroyuki Nagatomi, Office Action for Japanese Application No. 2008-322686, 4 pages, Dec. 8, 2011.

\* cited by examiner

*Primary Examiner* — Annette Dixon

(57) ABSTRACT

A continuous positive airway pressure system features a housing forming an airway chamber, and an air pressure inlet and an air pressure outlet. The housing further defines internally a pair of tapered air jets, and a pair of tapered air receivers. The air receivers are located downstream of the air supply jets and disposed coaxially with respective ones of the air supply jets. Each receiver has a taper in an opposite direction to the direction of the taper of the air supply jets. A pair of nasal prongs is located downstream of the air receiving jets.

14 Claims, 4 Drawing Sheets

CONTINUOUS POSITIVE AIRWAY PRESSURE DEVICE

FIELD OF THE INVENTION

The invention relates to pressure airway devices for supplying pressurized air used in the field of respiratory therapy, and more particularly to devices and methods that provide positive airway pressure to the nasal cannula of a person or particularly an infant.

BACKGROUND OF THE INVENTION

In the field of respiratory therapy it is known to provide a continuous positive airway pressure (CPAP) system and method for delivering continuous positive airway pressure, via the nasal cannula, to persons and particularly infants. This is particularly true in the case of prematurely born infants who frequently suffer with increased work of breathing due to immature lungs that have the propensity to collapse during exhalation and resist expansion during inhalation.

One particular method of treatment involves the use of nasal cannula that fits sealingly into the nares and are connected to a breathing system that generates a continuous flow of air with above atmospheric pressures, commonly referred to as continuous positive airway pressure (CPAP) therapy. The positive pressure is transmitted through the infant's airways and into the lungs thereby preventing collapse during exhalation and augmenting expansion during inhalation.

There are a wide variety of devices in use for CPAP. The CPAP devices often comprise what is referred to as a generator body, which is essentially a housing forming a chamber that receives air pressure from tubing. The generator body typically has an exhalation port for air to escape during the exhalation phase. Further, the generator body has a pair of nasal prongs which fit into the patient's nares to supply pressure into the nares.

It would be desirable to provide a CPAP device that has reduced size, improved performance, and/or other benefits with respect to the patient. Moreover, it is often desirable to be able to reduce the amount of pressure that needs to be supplied to a CPAP device, thereby simplifying the structure of the associated air pump, which may have benefits with respect to reduced size, energy consumption, sound, complexity and cost. Further, it is typically desirable to reduce the size and mass of the CPAP interface assembly which fits against the face. It may be desirable to have the head gear that attaches the CPAP device to be smaller, simpler and/or less cumbersome. It may also be advantageous to have such a device that facilitates handling of the patient by caretakers.

SUMMARY OF THE INVENTION

Some embodiments provide a CPAP device and method that has reduced size, improved performance, and/or other benefits with respect to the patient.

An aspect of the present invention in some embodiments involves a continuous positive airway pressure system, comprising a housing forming an airway chamber, and having an air pressure inlet and an air pressure outlet, and further defining internally a pair of tapered air jets; a pair of tapered air receivers each disposed coaxially with one of the air supply jets downstream of the air supply jets, and each having a taper in an opposite direction to the direction of taper of the air supply jets; and a pair of nasal prongs downstream of the air receivers.

Another aspect of the continuous positive airway pressure system in some embodiments comprises means for defining an airway chamber, and having an air pressure inlet and an air pressure outlet, and further defining internally a pair of tapered air jets; a pair of tapered air receiving means, each disposed coaxially with one of the air supply jets downstream of the air supply jets, and each having a taper in an opposite direction to the direction of taper of the air supply jets; and a pair of nasal interacting means downstream of the receiving means.

A further aspect of the present invention in some embodiments provides a continuous positive airway pressure method, providing air pressure to a housing forming an airway chamber, and further defining internally a pair of tapered air jets; directing air from the air jets to a pair of tapered air receivers, each disposed coaxially with one of the air supply jets downstream of the air supply jets, and each having a taper in an opposite direction to the direction of taper of the air supply jets; and directing air from the air receivers to a pair of nasal prongs downstream of the air receivers.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
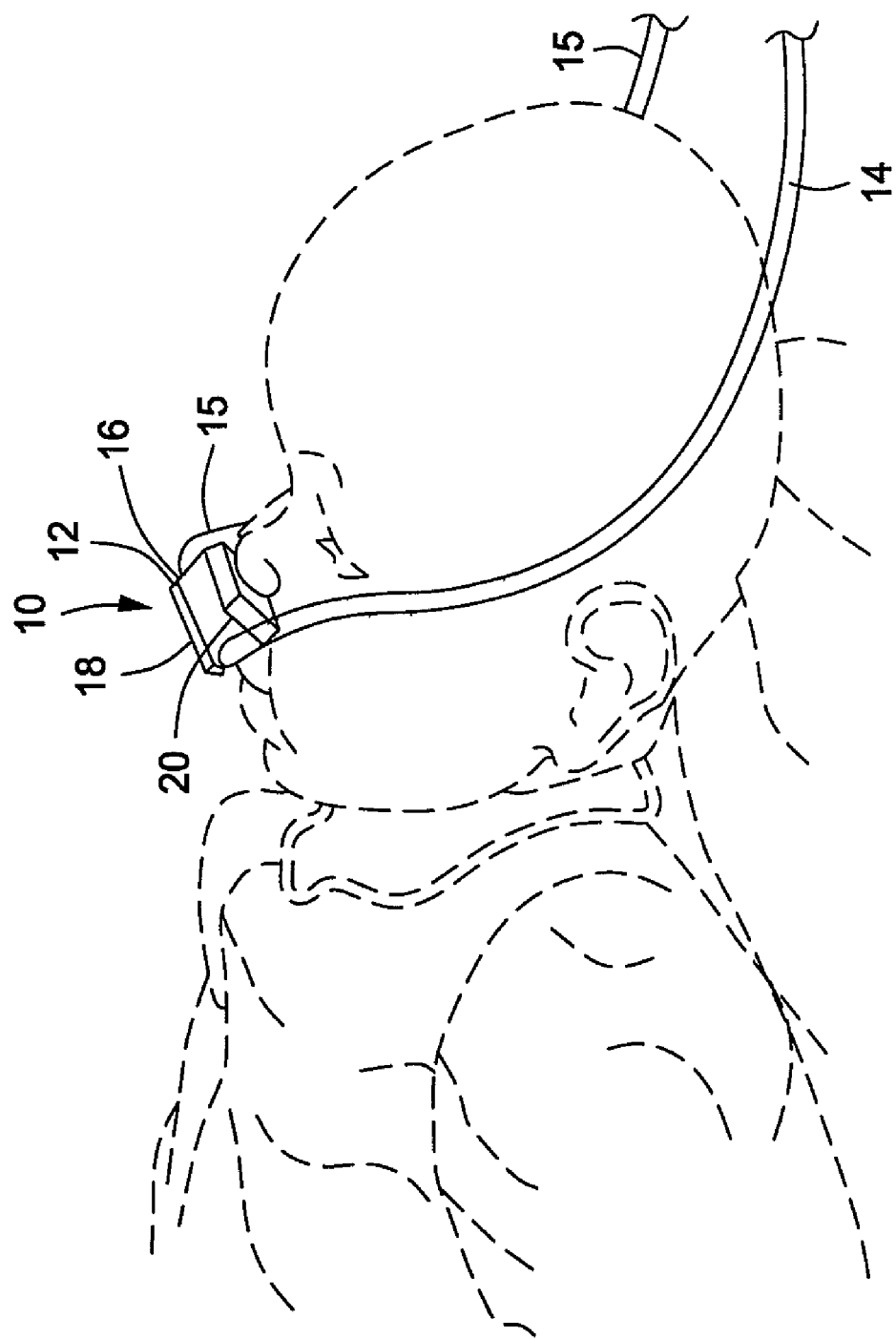
FIG. 1 is a perspective view of an infant patient also showing a CPAP device according to an embodiment of the present invention in use.

Some embodiments provide a CPAP device and method that has reduced size, improved performance, and/or other benefits with respect to the patient. Preferred embodiments of the invention will now be described with reference to the drawing Figures in which like reference numerals refer to like parts throughout.

FIG. 1 is a perspective view of a patient using a CPAP device according to an embodiment of the present invention. The device 10 includes a generator body 12 which receives positive airflow pressure from a supply tube 14. The tube 14 is pressurized by an air pressurize device which is not illustrated. The generator body 12 also is connected to an outlet tube 15. As will be seen in FIGS. 2 through 4, in a preferred embodiment the tubing for tubes 14 and 15 does not have a circular cross section, but rather has an oval or ellipsoid cross section. This oval cross section of the tubes 14 and 15 some times will provide a significant benefit, where used, in several respects. First, the oval tubing provides a greater volumetric area while still reducing the diameter of the tubing in one direction, and also allows for a more compact generator housing 16 as described in more detail below with respect to FIGS. 2 through 4. Second, the oval tubing has a tendency to lay flat if the patient turns his or her head and lies on the tubing. This relatively flat contact with the patient's head can be more comfortable and distribute the weight of the patient's head more evenly over the tubing as compared to circular tubing. However, some other aspects of the preferred embodiment that will be described below can still be obtained with the use of circular tubing.

FIG. 1 also illustrates, as will be seen in more detail in the subsequent Figures, that the generator body 12 includes a housing 16 (which has the inlet fitting 22 that connects to the tubing 14 and an outlet fitting 23 connected to the tubing 15) and also has an exhalation port 18 which permits outlet of the exhalation air. The housing 16 is attached to a receiver assembly 20 which includes prongs that fit into the patient's nares as will be described further below.

Figure 2:
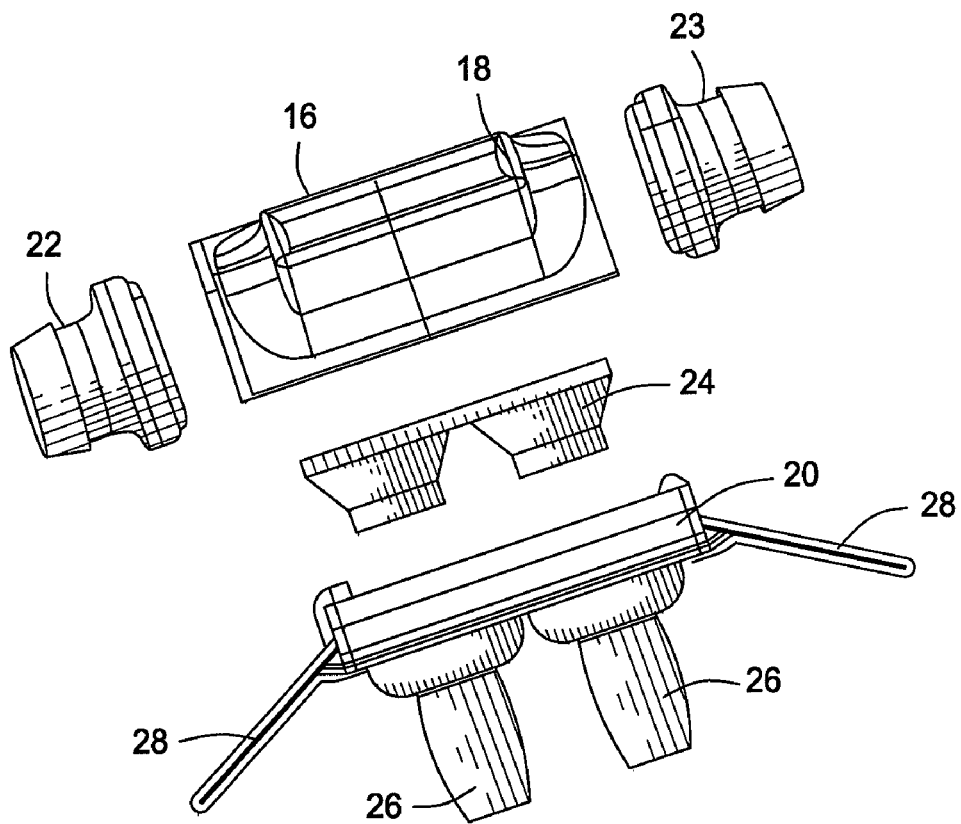
FIG. 2 is an exploded view of components of the CPAP device.
Figure 3:
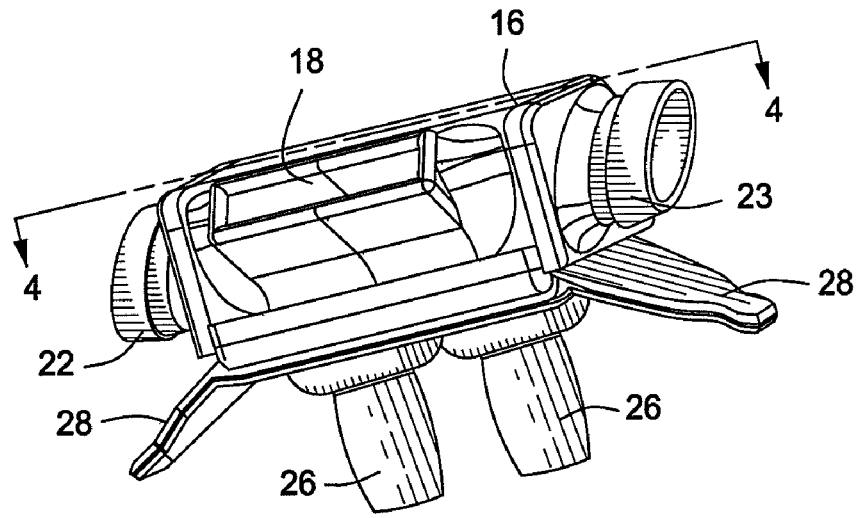
FIG. 3 is a perspective view of the device of FIG. 2 in an assembled condition.

Turning next to FIG. 2, the housing 16 and its exhalation port 18 are illustrated. The housing 16 is essentially a rectangular box-shaped housing having the exhalation port 18, and a pair of side structures on its side ends. The side structures each form sidewalls of the generator body and have the fittings 22 and 23 that receive the tubing 14 and 15, which is preferably oval tubing, as described above.

One side of the rectangular box shape of the housing 16 is open, and is adapted to receive a receiver assembly 20 which will be described in more detail below. When the receiver 20 is mounted to close off the open end of the housing 18, a receiver cap 24 is trapped inside. The receiver 20 includes a pair of nasal prongs 26 extending therefrom as well as a pair of headgear attachment flanges 28 projecting therefrom. The receiver nasal prongs 26 may be of any suitable size and shape as is suitable for interacting with the patient's nares. In addition, the headgear attachment flanges 28 may also be of any suitable size and shape to interact with a strap type headgear or an adhesive fastening arrangement, or any other type of patient attachment system.

Another advantage of the oval tubing 14 and 15 is that the housing 18 can have a relatively compact rectangular box shape, and the tubing 14 and 15 may be arranged with its major diameter at a diagonal angle, as can be seen by the orientation of the fittings 22 and 23, thus allowing the tubing 14 and 15 to have a major diameter that is nearly as long as the diagonal length of the profile of the housing 18. This contributes to the housing 18 having a desirably compact shape.

The assembly described above may be manufactured from any suitable materials. However, in one example, the housing 18 and its fittings 22 and 23, as well as the receiver cap 24, are manufactured from a plastic, such as a polycarbonate. The receiver 20, including the headgear attachment flanges, and nasal prongs, may be molded from a biocompatible silicone.

Figure 4:
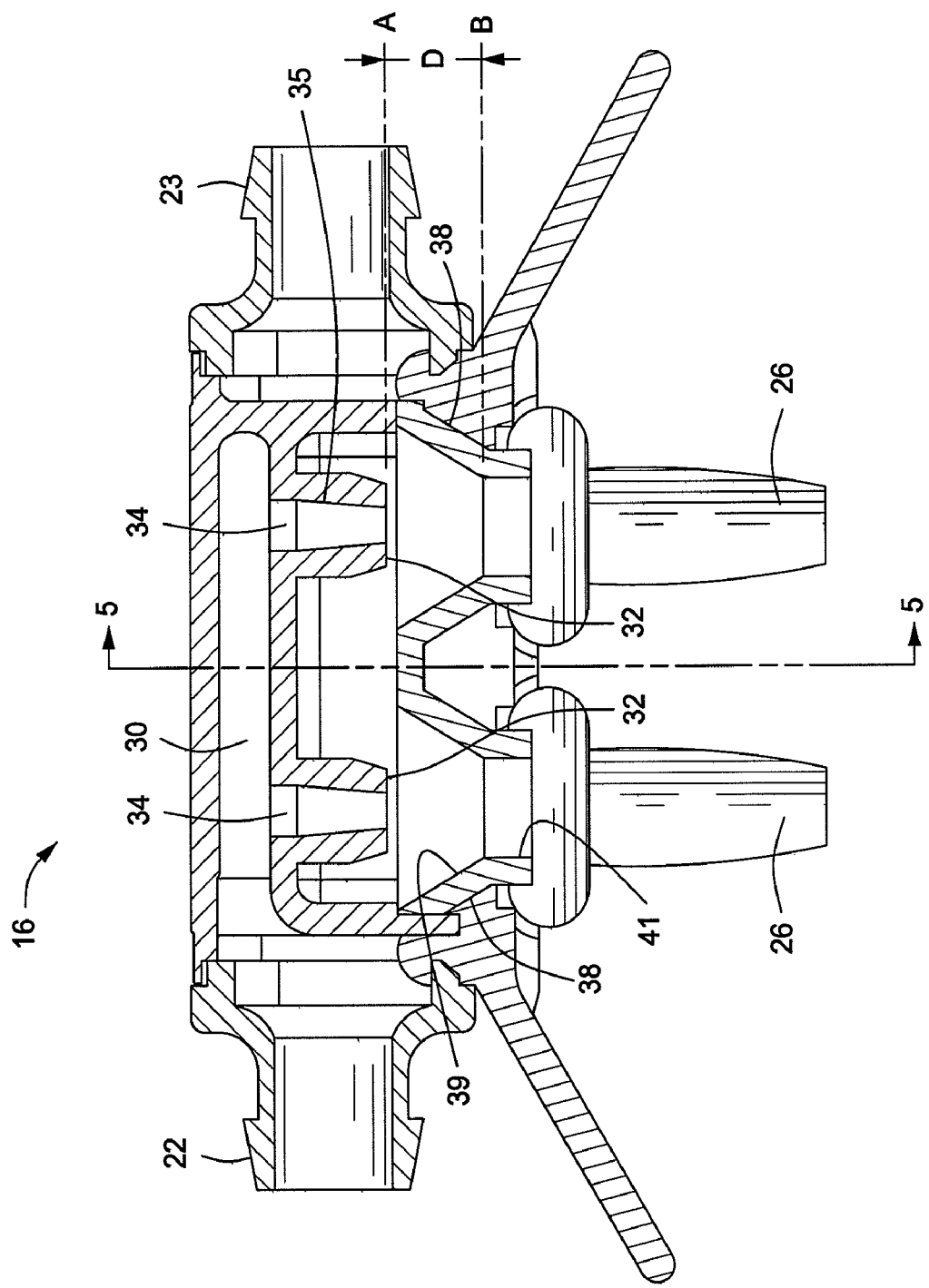
FIG. 4 is a cross sectional view taken through line 4-4 in FIG. 3 of the CPAP device of FIG. 3.
Figure 5:
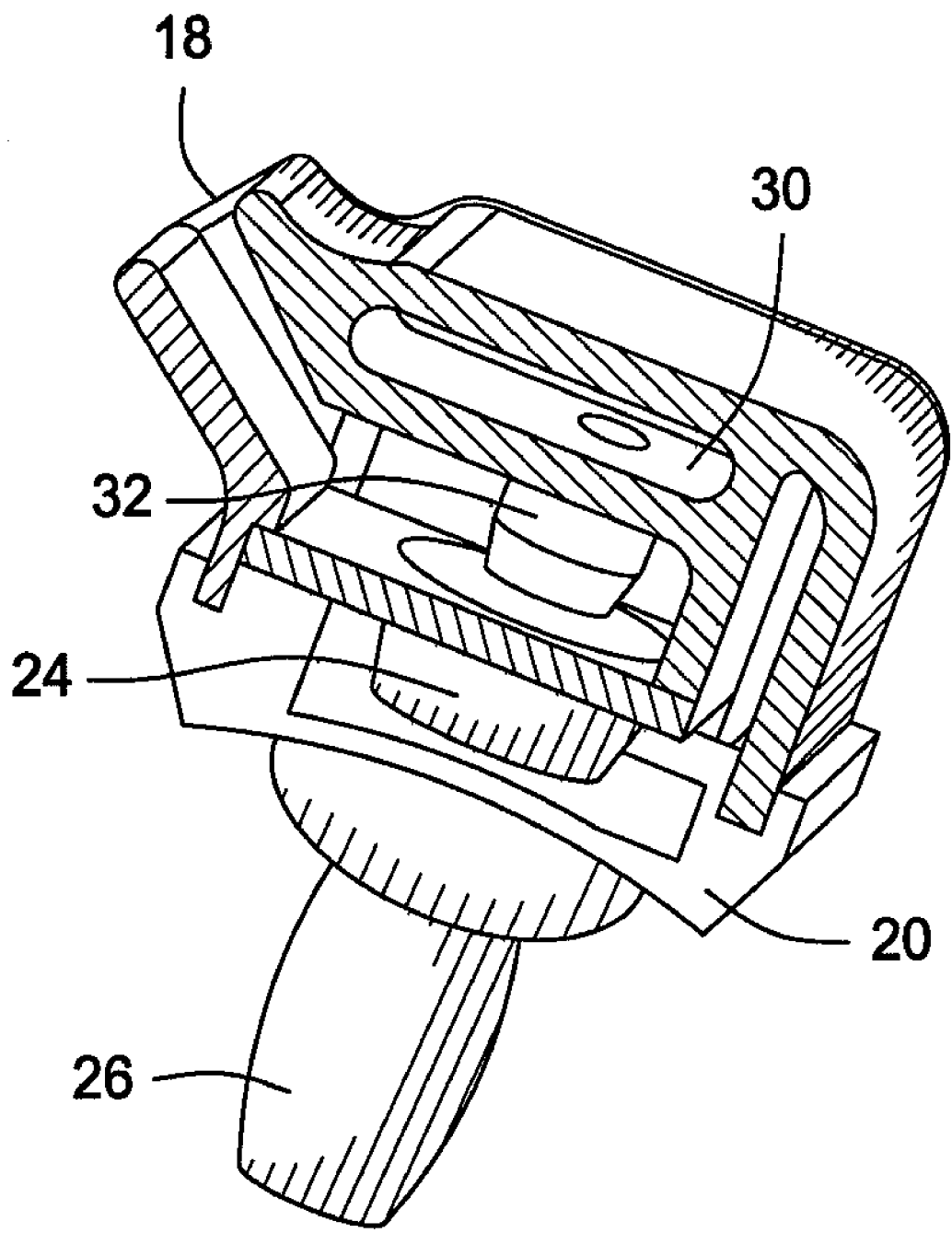
FIG. 5 is a cross sectional view taken through line 5-5 of FIG. 4, showing a cross section of the CPAP device of FIG. 3.

Turning next to FIGS. 4 and 5, the air flow within the CPAP device is illustrated. Supply air enters the housing 16 via a fitting 22 from a pressurized source through the tubing 14. The supply air enters a supply air channel 30 which feeds two supply air nozzle jets 32. Supply air nozzle jets 32 each generally have a first cylindrical portion 34 and then transition to a slight outward taper region 35. The tapered portion 35 is an outward flared conical taper with an included angle of approximately 4 degrees between the sidewalls. This outward taper has been found to provide a venturi effect which is beneficial to the airflow.

In addition to having a 4 degree included angle in the tapered portion 35, the axial length of the portion 35 is approximately two times the starting diameter, i.e., the internal diameter of the cylindrical portion 34 of the jet 32. This taper improves the efficiency of the nozzle and reduces the pressure required to drive the generator.

The jets 32 direct air towards the receiver cap assembly 24, and more particularly to two funnel shaped receivers 38. The nasal prongs 26 then receive air directly from the receivers 38. The receivers 38 each have a conically tapered portion 39 with an inward flared cone having an included angle of 60 degrees between the sidewalls. A straight cylindrical portion 41 extends from the end of the conical portion 39.

In one preferred embodiment, a distance D from a reference line A, which is the outlet end face 36 of the jet 32 relative to reference line B, which is the end face of the conical portion of the receivers 38, has been found to be 1.8 times the internal diameter of the cylindrical portion 34 of the jets 32.

The outlet fitting 23 leads to outlet tubing by which the patient pressure can be monitored at an outlet side of the device, i.e., pressure monitoring system that is not shown.

FIG. 5 is a cross section view showing at a different angle some of the various components referred to above using the same reference numerals.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A continuous positive airway pressure system, comprising:
    a housing forming an airway chamber, and having an air pressure inlet and an air pressure outlet, and further defining internally a pair of tapered air jets, each of said pair of tapered jets comprising a first opening fluidly coupled with said air pressure inlet and tapering to a second opening, smaller than said first opening, wherein said second opening is downstream of said first opening;
    a pair of tapered air receivers each disposed coaxially with one of the tapered air jets downstream of the tapered air jets, and each having a taper in an opposite direction to the direction of taper of the tapered air jets, each of said pair of tapered air receivers comprising a first opening fluidly coupled with one of said pair of tapered jets and tapering to a second opening, smaller than said first opening, wherein said second opening is downstream of said first opening, and wherein said first opening of one of said pair of tapered air receivers faces said second opening of one of said pair of tapered jets; and a pair of nasal prongs downstream of the pair of tapered air receivers.

2. The system of claim 1, wherein the tapered air jets each have a portion with an outward taper in the direction of air flow.

3. The system of claim 2, wherein the outward tapered portions of the tapered air jets each have an included angle of approximately 4 degrees.

4. The system of claim 1, wherein the pair of tapered air receivers each have a portion with an inward taper in the direction of air flow.

5. The system of claim 4, wherein the inward tapered portion of the pair of tapered air receivers each have an included angle of approximately 30 degrees.

6. The system of claim 1, wherein the tapered air jets each have a portion having a minimum internal diameter of the tapered air receiver, and a terminal end face, and wherein the tapered portion of the air receivers has a terminal downstream end, and wherein a distance between the terminal end face of the tapered air jets and the terminal downstream end is approximately 1.8 times the minimum internal diameter of the tapered air jets.

7. The system of claim 1, wherein the housing includes an inlet fitting that is adapted to receive tubing for supply air.

8. The system of claim 1, wherein the housing has an outlet fitting that is adapted to receive tubing so that internal pressure in the chamber of the body may be measured via the outlet fitting.

9. A method of providing continuous positive airway pressure system, comprising:

providing air pressure to a housing forming an airway chamber, and further defining internally a pair of tapered air jets, each of said pair of tapered jets comprising a first opening fluidly coupled with said air pressure inlet and tapering to a second opening, smaller than said first opening, wherein said second opening is downstream of said first opening;

directing air from the tapered air jets to a pair of tapered air receivers, each disposed coaxially with one of the air supply jets downstream of the air supply jets, and each having a taper in an opposite direction to the direction of taper of the tapered air supply jets, each of said pair of tapered air receivers comprising a first opening fluidly coupled with one of said pair of tapered lets and tapering to a second opening, smaller than said first opening, wherein said second opening is downstream of said first opening, and wherein said first opening of one of said pair of tapered air receivers faces said second opening of one of said pair of tapered jets; and directing air from the tapered air receivers to a pair of nasal prongs downstream of the tapered air receivers.

10. The method of claim 9, wherein the tapered air jets each have a portion with an outward taper in the direction of air flow.

11. The method of claim 10, wherein the outward tapered portions of the tapered air jets each have an included angle of approximately 4 degrees.

12. The method of claim 9, wherein the tapered air receivers each have a portion with an inward taper in the direction of air flow.

13. The method of claim 12, wherein the inward tapered portion of the tapered air receivers each have an included angle of approximately 30 degrees.

14. The method of claim 9, wherein the tapered air jets each have a portion having a minimum internal diameter of the tapered air receivers, and a terminal end face, and wherein the tapered portion of the tapered air receivers has a terminal downstream end, and wherein a distance between the terminal end face of the tapered air jets and the terminal downstream end is approximately 1.8 times the minimum internal diameter of the tapered air jets.

\* \* \* \* \*

UNITED STATES PATENT AND TRADEMARK OFFICE
CERTIFICATE OF CORRECTION

Page 1 of 1

PATENT NO. : 8,210,182 B2
APPLICATION NO. : 11/966805
DATED : July 3, 2012
INVENTOR(S) : Steven Duquette and Steve Han It is certified that error appears in the above-identified patent and that said Letters Patent is hereby corrected as shown below:

Column 6, Claim 9, Line 10: Delete "coupled with one of said pair of tapered lets and tapering"
Insert -- coupled with one of said pair of tapered jets and tapering --

Signed and Sealed this
Eighteenth Day of December, 2012

David J. Kappos
*Director of the United States Patent and Trademark Office*